United States Patent
Suprise et al.

(10) Patent No.: US 6,174,303 B1
(45) Date of Patent: Jan. 16, 2001

(54) DISPOSABLE ABSORBENT ARTICLE HAVING A DUAL FASTENING SYSTEM

(75) Inventors: Jody Dorothy Suprise, Pine River; Barbara Ann Owen, Menasha, both of WI (US)

(73) Assignee: Kimberly-Clark Worldwide, Neenah, WI (US)

(*) Notice: Under 35 U.S.C. 154(b), the term of this patent shall be extended for 0 days.

(21) Appl. No.: 08/938,677

(22) Filed: Sep. 26, 1997

(51) Int. Cl.$^7$ ................................................. A61F 13/15
(52) U.S. Cl. .................... 604/385.29; 604/385.25; 604/385.3; 604/391; 604/398
(58) Field of Search .................. 604/385.1–386, 604/391–401, 385.01, 385.22, 385.24, 385.25, 385.29, 385.3; 602/70

(56) References Cited

U.S. PATENT DOCUMENTS

| | | |
|---|---|---|
| H1558 | 7/1996 | Goulait et al. ............... 156/210 |
| D. 290,780 | 7/1987 | Wistrand ........................ D2/10 |
| 1,963,334 | 6/1934 | Neilson .............................. 2/237 |
| 2,466,184 * | 4/1949 | Riggs ............................ 604/398 |
| 2,475,175 | 7/1949 | Cadous ............................. 2/237 |
| 2,477,914 | 8/1949 | Webb . |
| 2,545,761 | 3/1951 | Brink . |
| 2,570,963 | 10/1951 | Mesmer . |
| 2,630,120 | 3/1953 | Nielson . |
| 2,743,725 | 5/1956 | Matthews . |
| 2,830,589 | 4/1958 | Doner . |
| 2,833,282 | 5/1958 | Moore . |
| 2,910,982 | 11/1959 | Woodward . |
| 2,931,361 | 4/1960 | Sostrin . |
| 3,592,194 | 7/1971 | Duncan . |
| 3,882,871 | 5/1975 | Taniguchi . |
| 4,074,716 | 2/1978 | Schaar . |
| 4,205,679 | 6/1980 | Repke et al. . |
| 4,500,316 | 2/1985 | Damico ............................ 604/389 |
| 4,581,772 | 4/1986 | Smith ................................ 2/111 |
| 4,596,055 | 6/1986 | Aach et al. ...................... 2/237 |

(List continued on next page.)

FOREIGN PATENT DOCUMENTS

| | | |
|---|---|---|
| 93/38590 | 11/1993 | (AU) . |
| 0 217 032 | 4/1987 | (EP) . |
| 0 382 022 | 8/1990 | (EP) . |
| 0 605 012 | 7/1994 | (EP) . |
| 0 544 703 | 9/1994 | (EP) . |
| 0 753 292 | 1/1997 | (EP) . |
| 1 520 740 | 8/1978 | (GB) . |
| 2 242 612 | 10/1991 | (GB) . |
| 2 288 314 | 10/1995 | (GB) . |
| 2 288 315 | 10/1995 | (GB) . |
| 2 288 316 | 10/1995 | (GB) . |
| 2 294 867 | 5/1996 | (GB) . |
| 2 297 473 | 6/1996 | (GB) . |
| 6-77718 | 11/1994 | (JP) . |

* cited by examiner

Primary Examiner—John G. Weiss
Assistant Examiner—K. M. Reichle
(74) Attorney, Agent, or Firm—Jeffrey B. Curtin (57) ABSTRACT

A disposable absorbent article defines an outer cover, an absorbent chassis and a dual fastening system. The dual fastening system includes a pair of primary fasteners located on the outer cover in one of the waist regions of the absorbent article and a pair of secondary fasteners located on the outer cover in the opposite waist region of the absorbent article. The primary fasteners are configured to engage an outer surface of the absorbent article to maintain the article about the waist of the wearer and the secondary fasteners are configured to engage a body facing surface of the absorbent chassis to support the absorbent chassis. The absorbent chassis is attached to the outer cover at the waist edges and remains at least partially unattached from the outer cover between the waist edges to allow the outer cover to have a blousy appearance. Thus, the disposable absorbent article has an aesthetically pleasing garment-like appearance and improved fit and containment during use.

25 Claims, 3 Drawing Sheets

U.S. PATENT DOCUMENTS

| | | |
|---|---|---|
| 4,610,680 | 9/1986 | LaFleur . |
| 4,615,695 | 10/1986 | Cooper . |
| 4,617,022 | 10/1986 | Pigneul et al. ................... 604/391 |
| 4,663,220 | 5/1987 | Wisneski et al. .................. 428/221 |
| 4,704,116 | 11/1987 | Enloe . |
| 4,747,846 | 5/1988 | Boland et al. . |
| 4,753,650 | 6/1988 | Williams ........................... 604/389 |
| 4,798,603 | 1/1989 | Meyer et al. ...................... 604/378 |
| 4,826,499 | 5/1989 | Ahr .................................... 604/389 |
| 4,834,736 * | 5/1989 | Boland et al. ................... 604/385.2 |
| 4,850,988 | 7/1989 | Aledo et al. ..................... 604/385.1 |
| 4,850,992 | 7/1989 | Amaral et al. ..................... 604/389 |
| 4,883,481 | 11/1989 | Blanchard ....................... 604/385.1 |
| 4,892,598 * | 1/1990 | Stevens et al. ..................... 604/397 |
| 4,904,252 | 2/1990 | Fitzgerald ....................... 604/385.1 |
| 4,944,733 | 7/1990 | Casale ............................ 604/385.1 |
| 4,988,346 | 1/1991 | Pfefferkorn ........................ 604/389 |
| 4,998,929 | 3/1991 | Bjorksund et al. .............. 604/385.2 |
| 5,026,364 * | 6/1991 | Robertson ....................... 604/385.2 |
| 5,062,839 | 11/1991 | Anderson ....................... 604/385.1 |
| 5,069,672 * | 12/1991 | Wippler et al. .................... 604/398 |
| 5,069,678 | 12/1991 | Yamamoto et al. ............. 604/385.2 |
| 5,087,253 | 2/1992 | Cooper ........................... 604/385.1 |
| 5,106,382 | 4/1992 | Henry ............................. 604/385.2 |
| 5,151,092 * | 9/1992 | Buell et al. ...................... 604/385.1 |
| 5,176,668 | 1/1993 | Bernardin ......................... 604/368 |
| 5,176,672 | 1/1993 | Bruemmer et al. ............. 604/385.1 |
| 5,185,011 | 2/1993 | Strasser ........................... 604/385.1 |
| 5,187,817 * | 2/1993 | Zolner .............................. 604/393 |
| 5,192,606 | 3/1993 | Proxmire et al. ................... 428/284 |
| 5,226,992 | 7/1993 | Morman ............................. 156/62.4 |
| 5,242,436 | 9/1993 | Weil et al. ...................... 604/385.2 |
| 5,304,162 | 4/1994 | Kuen ................................. 604/391 |
| 5,358,500 | 10/1994 | Lavon et al. .................... 604/385.2 |
| 5,368,584 | 11/1994 | Clear et al. ..................... 604/385.2 |
| 5,368,585 | 11/1994 | Dokken ............................. 604/393 |
| 5,370,632 | 12/1994 | Beplate .......................... 604/385.1 |
| 5,370,634 | 12/1994 | Ando et al. ..................... 604/385.1 |
| 5,373,587 | 12/1994 | Sexton ................................. 2/237 |
| 5,374,262 | 12/1994 | Keuhn, Jr. et al. ................ 604/391 |
| 5,383,872 | 1/1995 | Roessler et al. .................... 604/391 |
| 5,386,595 | 2/1995 | Kuen et al. ........................... 2/400 |
| 5,389,095 | 2/1995 | Suzuki et al. ................... 604/385.2 |
| 5,397,639 | 3/1995 | Tollini ............................... 428/343 |
| 5,423,789 | 6/1995 | Kuen ................................. 604/386 |
| 5,462,541 | 10/1995 | Bruemmer et al. ................ 604/391 |
| 5,489,282 | 2/1996 | Zehner et al. .................. 604/385.1 |
| 5,499,978 | 3/1996 | Buell et al. ..................... 604/385.2 |
| 5,509,915 | 4/1996 | Hanson et al. ..................... 604/378 |
| 5,527,302 | 6/1996 | Endres et al. ................... 604/385.1 |
| 5,531,732 | 7/1996 | Wood ................................. 604/391 |
| 5,569,232 | 10/1996 | Roe et al. ....................... 604/385.2 |
| 5,569,234 | 10/1996 | Buell et al. ........................ 604/396 |
| 5,575,785 | 11/1996 | Gryskiewicz et al. ........... 604/385.2 |
| 5,591,152 | 1/1997 | Buell et al. ..................... 604/385.2 |
| 5,593,401 | 1/1997 | Sosalla et al. .................. 604/385.2 |
| 5,607,416 | 3/1997 | Yamamoto et al. ................ 604/397 |
| 5,624,428 | 4/1997 | Sauer ............................... 604/391 |
| 5,695,488 * | 12/1997 | Sosalla ............................ 604/385.2 |

DISPOSABLE ABSORBENT ARTICLE HAVING A DUAL FASTENING SYSTEM

FIELD OF THE INVENTION

The present invention relates to disposable absorbent articles which are adapted to contain body exudates. More particularly, the present invention relates to disposable absorbent articles which have fastening systems to maintain the articles about the waist of the wearer.

BACKGROUND OF THE INVENTION

Conventional disposable absorbent articles, such as disposable diapers, have typically included a bodyside liner, an outer cover, and an absorbent core disposed between the outer cover and the bodyside liner. The articles have generally defined a front waist region, a rear waist region and a crotch region which extends between and connects the front and rear waist regions. Such conventional absorbent articles have also included fastening systems which are configured to secure the article on the wearer's waist. The absorbent articles have also been constructed with various types of elasticized portions at the waist and leg opening regions. Such elasticized portions have been used to reduce the leakage of body exudates from the absorbent article and improve the appearance and fit of the absorbent article about the wearer.

Typically, the fastening systems on conventional absorbent articles have included a pair of fasteners located on the outermost corners of the absorbent article in one of the waist regions of the article. Such fasteners have been configured to releasably engage a complimentary fastener in the opposite waist region of the absorbent article. For example, the fastening systems have included a pair of fasteners, such as adhesive tape tabs, located on the outermost corners of the absorbent article in the rear waist region of the article. Such systems have also included a complimentary fastener, such as a taping panel, located on the outer surface of the outer cover of the absorbent article in the front waist region of the article. In such a configuration, the absorbent article has been positioned between the legs of the wearer and the adhesive tape tabs have been releasably attached to the taping panel to secure the absorbent article about the waist of the wearer.

However, conventional disposable absorbent articles which are configured as described above have exhibited several shortcomings. For example, it has been difficult to maintain and conform conventional absorbent articles and, in particular, the absorbent cores of such articles about the body of the wearer. Typically, the absorbent core on such conventional absorbent articles has been bonded to or immobilized between the outer cover and the bodyside. However, the absorbent cores on such articles have sagged or drooped especially after becoming saturated with body exudates. Such sagging and drooping has undesirably resulted in improper fit and appearance which has lead to increased leakage. Moreover, the outer covers on such absorbent articles have not had a "blousy" appearance in use.

In an attempt to better gather the absorbent core and the absorbent article, the waist and leg opening regions of conventional absorbent articles have included elastics which apply high contracting or gathering forces on the absorbent article. However, such high forces have undesirably resulted in irritation and red marking of the skin of the wearer. The high forces have also resulted in an undesirable level of bunching of the absorbent article especially in the crotch region which has not been aesthetically pleasing.

Despite the attempts to develop more aesthetically pleasing and improved disposable absorbent articles, there remains the need for disposable absorbent articles which contain body exudates while providing an optimum fit about the wearer and maintaining a pleasing appearance even after becoming saturated. Moreover, there is a need for disposable absorbent articles which have a garment-like appearance and which can be easily secured about and removed from the waist of a wearer.

SUMMARY OF THE INVENTION

In response to the difficulties and problems discussed above, a new disposable absorbent article which has a loose fitting outer cover to provide a more garment-like appearance has been discovered. In one aspect, the present invention concerns a disposable absorbent article which defines a front waist region, a back waist region and a crotch region which extends between and connects the waist regions. The absorbent article includes an outer cover, an absorbent chassis and a dual fastening system which includes a pair of primary fasteners located on the outer cover in one of the waist regions of the absorbent article and a pair of secondary fasteners located on the outer cover in the opposite waist region of the absorbent article. The primary fasteners are configured to engage an outer surface of the absorbent article and the secondary fasteners are configured to engage a body facing surface of the absorbent chassis in use. In a particular embodiment, the absorbent chassis defines a front attached portion and a back attached portion which are attached to the outer cover and an unattached portion which extends between and connects the attached portions and which remains substantially unattached to the outer cover.

In another aspect, the present invention concerns a disposable absorbent article which defines a front waist region, a back waist region and a crotch region which extends between and connects the waist regions. The absorbent article includes an outer cover, an absorbent chassis and a dual fastening system. The absorbent chassis includes a backsheet, a bodyside liner which is connected to the backsheet in a superposed relation and an absorbent core disposed between the backsheet and the bodyside liner. At least about 90 percent of a length of the absorbent chassis remains substantially unattached to the outer cover. The dual fastening system includes a pair of primary fasteners which are located on the outer cover in one of the waist regions of the absorbent article and which are configured to engage an outer surface of the absorbent article. The dual fastening system also includes a pair of secondary fasteners which are located on the outer cover in the opposite waist region of the absorbent article and which are configured to engage the bodyside liner of the absorbent chassis in use.

In yet another aspect, the present invention concerns a disposable absorbent article which defines a front waist region, a back waist region and a crotch region which extends between and connects the waist regions. The absorbent article includes an outer cover, an absorbent chassis which is connected to the outer cover in superposed relation and which defines a pair of longitudinally opposed waist edges, a waist flap connected to one of the waist edges of the absorbent chassis, and a dual fastening system. The dual fastening system includes a pair of primary fasteners which are located on the outer cover in the one waist region of the absorbent article and which are configured to engage an outer surface of the absorbent article. The dual fastening system also includes a pair of secondary fasteners which are located on the outer cover in the opposite waist region of the absorbent article and which are configured to engage a body facing surface of the waist flap in use. In a particular embodiment, at least about 90 percent of a length of the absorbent chassis remains substantially unattached to the outer cover.

The present invention advantageously provides a disposable absorbent article which has a garment-like appearance and refastenable side seams which allow the article to be easily secured about and removed from the waist of the wearer. The disposable absorbent article of the different aspects of the present invention also achieves a good fit while maintaining an aesthetically pleasing appearance when compared to conventional absorbent articles which gather and bunch in the crotch region. Moreover, the disposable absorbent article of the present invention provides improved containment of body exudates within the absorbent core of the article by allowing the absorbent core to remain unattached from the outer cover in at least the crotch region of the article and maintaining the absorbent core close to the wearer's body during use.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns disposable absorbent articles which have a garment-like appearance and an improved fastening system. The disposable absorbent articles are adapted to be worn adjacent to the body of a wearer to absorb and contain various exudates discharged from the body. As used herein, the term "disposable" refers to articles which are intended to be discarded after a limited use and which are not intended to be laundered or otherwise restored for reuse. The disposable absorbent articles of the present invention will be described in terms of a disposable diaper article which is adapted to be worn by infants about the lower torso. It is understood that the disposable absorbent articles of the present invention are equally adaptable for use as other types of absorbent articles such as adult incontinent products, training pants, feminine hygiene products, other personal care or health care garments, and the like.

Figure 1:
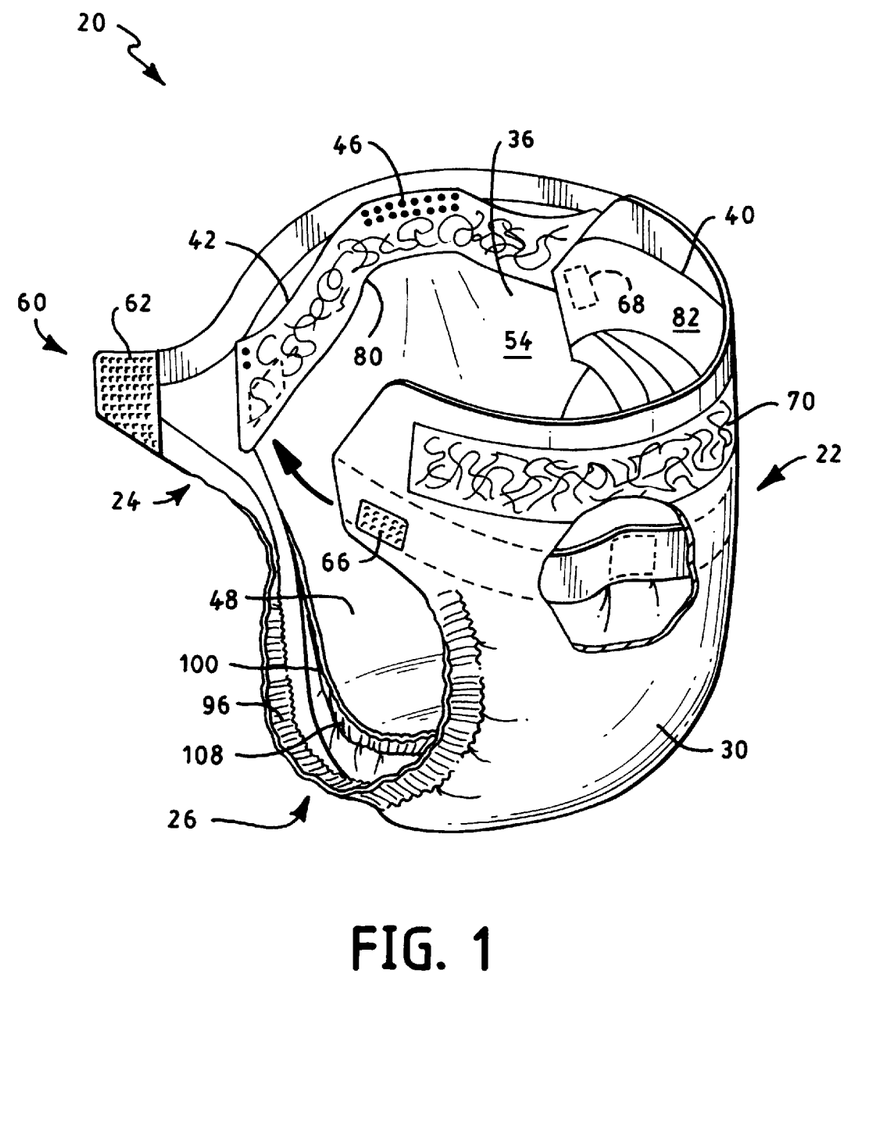
FIG. 1 representatively shows a partially cut-away, perspective view of an example of a disposable absorbent article according to the present invention wherein the elastic members have contracted and gathered the edges of the disposable absorbent article.
Figure 2:
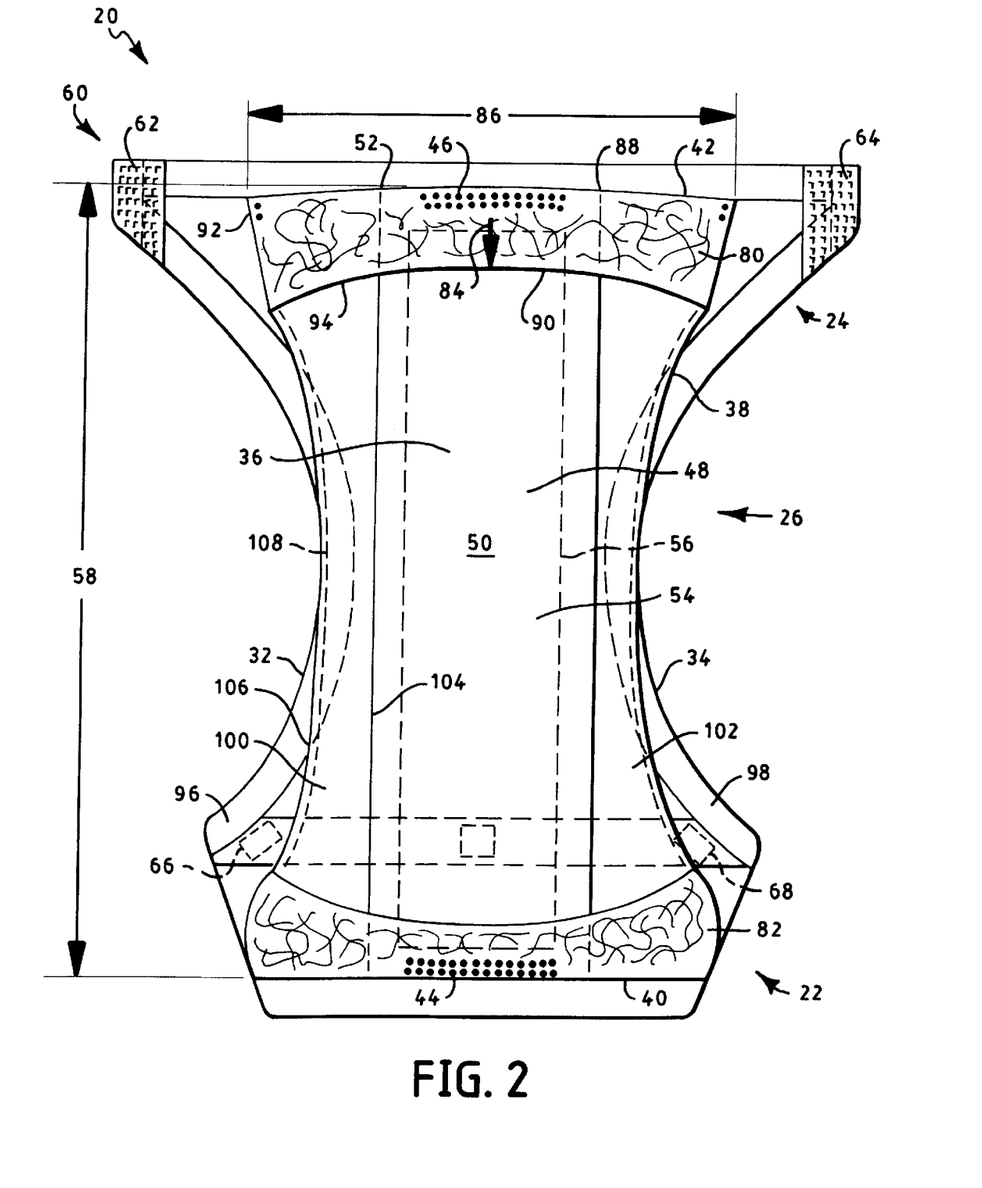
FIG. 2 representatively shows a plan view of the disposable absorbent article of FIG. 1 in a stretched and laid flat condition with the surface of the article which contacts the wearer facing the viewer.
Figure 3:
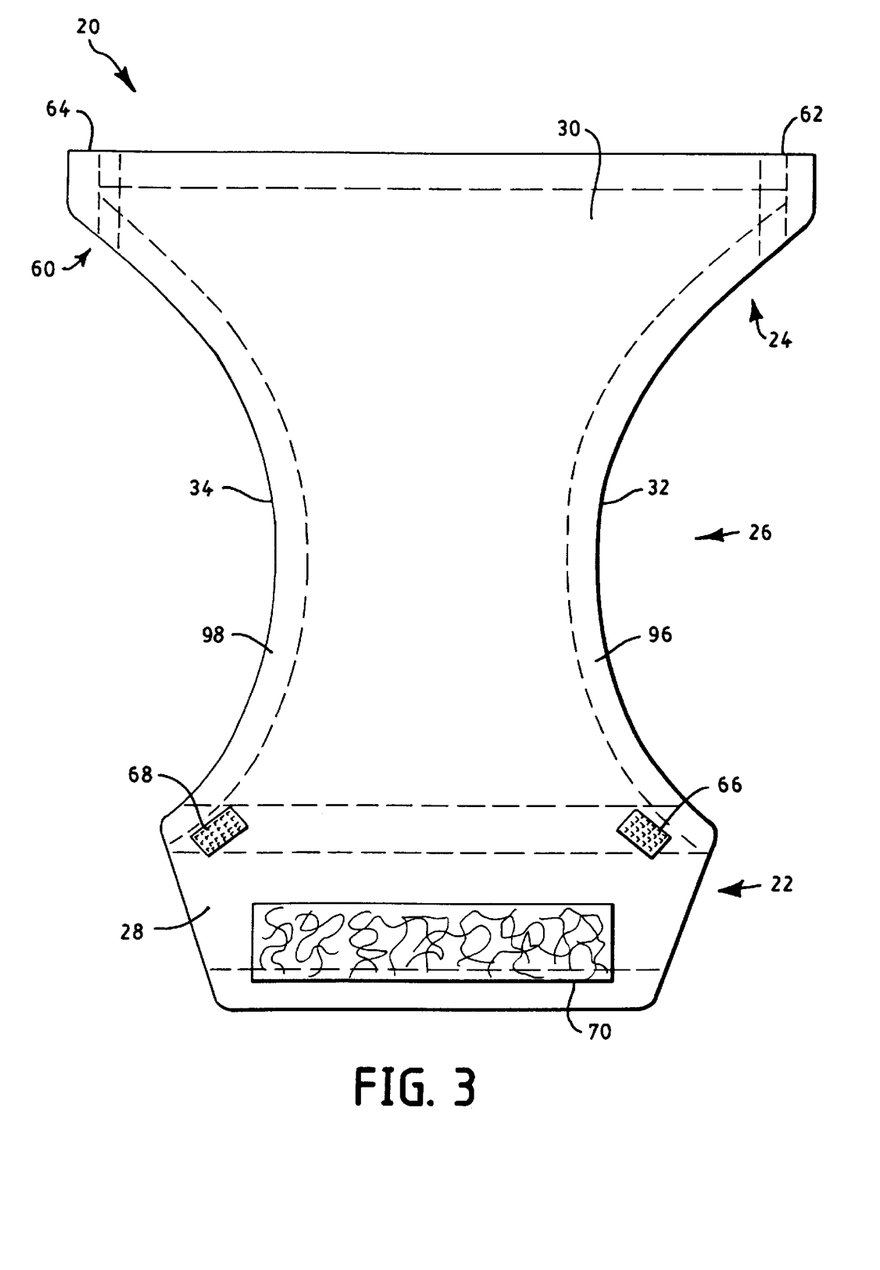
FIG. 3 representatively shows a plan view of the disposable absorbent article of FIG. 1 in a stretched and laid flat condition with the surface of the article which contacts the wearer's clothing facing the viewer.

FIGS. 1–3 representatively illustrate an example of a disposable diaper, as generally indicated at 20, according to the present invention. As representatively illustrated in FIGS. 1–3, the diaper 20 defines a front waist region 22, a rear waist region 24 and a crotch region 26 which extends between and connects the front and rear waist regions 22 and 24. The diaper 20 also defines an outer surface 28 which is configured to contact a wearer's garments in use. The front waist region 22 comprises the portion of the diaper 20 which, when worn, is positioned on the front of the wearer while the rear waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer.

The diaper 20 includes an outer cover 30, an absorbent chassis 36 and a dual fastening system 60 which includes a pair of primary fasteners 82 and 64 and a pair of secondary fasteners 66 and 68. The absorbent chassis 36 is configured to contain and/or absorb any body exudates discharged from the wearer. Whereas, the outer cover 30 and dual fastening system 60 are configured to maintain the diaper 20 about the waist of the wearer, conceal the absorbent chassis 36 from view, and provide a garment-like appearance. The diaper 20 may further include leg elastics 96 and 98 and containment flaps 100 and 102. It should be recognized that individual components of the diaper 20 may be optional depending upon the intended use of the diaper 20.

As representatively illustrated in FIGS. 1–3, the outer cover 30 of the diaper 20 defines a pair of laterally opposed side edges 32 and 34 which define leg openings which may be curvilinear. The outer cover 30 also defines a waist opening which is configured to encircle the waist of the wearer when worn. The outer cover 30 of the diaper 20 may suitably be composed of a material which is either liquid permeable or liquid impermeable. Since the absorbent chassis 36 of the different aspects of the present invention is designed to contain the body exudates discharged from the wearer, it is generally not necessary that the outer cover 30 be liquid impermeable. For example, the outer cover 30 may include various woven or nonwoven materials such as spunbond material, meltblown material, cotton material, rayon material or combinations thereof such as a spunbond-meltblown-spunbond (SMS) laminate material.

The outer cover 30 may otherwise be at least partially liquid impermeable to further prevent any leakage of body exudates. For example, a typical outer cover 30 can be manufactured from a thin plastic film or other flexible liquid-impermeable material. In a particular aspect, the outer cover 30 may be formed from a polyethylene film having a thickness of from about 0.012 millimeter (0.5 mil) to about 0.051 millimeter (2.0 mils). The outer cover 30 may also be formed of a woven or nonwoven fibrous web layer which has been totally or partially constructed or treated to impart a desired level of liquid impermeability to selected regions. Further, the outer cover 30 may optionally be composed of a micro-porous "breathable" material which permits vapors to escape from the diaper 20 while still preventing liquid exudates from passing through the outer cover 30. Still further, the outer cover 30 may also be an elasticized material such as a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference.

If it is desired to present the outer cover 30 with a more clothlike feeling, the outer cover 30 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). The outer cover 30 may otherwise be a stretch-thermal laminate (STL) material which includes a film layer positioned between two spunbond layers and which has a basis weight of about 70–75 grams per square meter. The film layer may be composed of meltblown polypropylene fibers and the spunbond layers may be composed of polypropylene fibers.

The outer cover 30 may also include bicomponent fibers such as polyethylene/polypropylene bicomponent fibers. Methods of forming such clothlike outer covers are known to those skilled in the art.

The outer cover 30 of the diaper 20 may also include a pair of concealment cuffs (not shown) which are configured to hide the absorbent chassis 36 and provide an additional barrier to the lateral flow of body exudates. The concealment cuffs may be located along the laterally opposed side edges 32 and 34 of the outer cover 30. The construction of such concealment cuffs is generally known to those skilled in the art. For example, the concealment cuffs may be constructed of a material which is similar to the material comprising the outer cover 30 and may be attached to the side edges 32 and 34 of the outer cover 30 to effectively hide or conceal the absorbent chassis 36 from view. Generally, each concealment cuff includes a fixed edge which is attached to the side edges 32 and 34 of the outer cover 30 and a free edge which tends to position itself in a spaced relation away from the outer cover 30 toward a generally upright and perpendicular configuration, especially in the crotch region 26 when in use. Desirably, the free edge of each concealment cuff maintains a contacting relationship with the body of the wearer while the outer cover 30 may be spaced away from the body of the wearer when in use. Typically, an elastic member is attached to the free edge of each concealment cuff to maintain the spaced away relationship between the free edge and the outer cover 30.

As representatively illustrated in FIGS. 1–3, the absorbent chassis 36 of the diaper 20 of the present invention defines a pair of laterally opposed side edges 38, a front waist 30 edge 40 and a rear waist edge 42. The absorbent chassis 36 of the present invention is suitably connected to the outer cover 30 to provide the disposable diaper 20. As representatively illustrated in FIGS. 1–3, the absorbent chassis 36 is desirably connected to the outer cover 30 only at or adjacent the waist edges 40 and 42 of the absorbent chassis 36 thereby creating a front attached portion 44, a rear attached portion 46 and an unattached portion 48 which extends between and connects the attached portions 44 and 46. The unattached portion 48 of the absorbent chassis 36 remains substantially unattached to the outer cover 30 and is generally configured to fit between the legs of the wearer and at least partially cover the lower torso of the wearer when in use. As a result, the unattached portion 48 is generally the portion of the absorbent chassis 36 which is configured to initially receive the body exudates from the wearer when in use.

The absorbent chassis 36 is connected to the outer cover 30 in such a manner to secure the chassis 36 in place while not adversely restricting the movement of the outer cover 30 in use. For example, the absorbent chassis 36 may be connected to the outer cover 30 along a longitudinal length of no more than about 5.1 centimeters and desirably no more than about 1.3 centimeters at each of the waist edges 40 and 42 of the absorbent chassis 36. In one aspect, the absorbent chassis 36 is connected to the outer cover 30 such that the unattached portion 48 of the absorbent chassis 36 defines a longitudinal length of at least about 90 percent and desirably at least about 95 percent of a length 58 of the absorbent chassis 36. In such a configuration, the absorbent chassis 36 more readily conforms to the body and movements of the wearer in use without adversely affecting the garment-like appearance of the outer cover 30. In a particular aspect, the longitudinal length of the unattached portion 48 of the absorbent chassis 36 is less than the longitudinal length of the outer cover 30 between the attached portions 44 and 46. In such a configuration, the absorbent chassis 36 maintains a spaced away relationship from the outer cover 30 in at least the crotch region 26 when in use.

The absorbent chassis 36 may be suitably connected to the outer cover 30 to form the diaper 20 using any means known to those skilled in the art. For example, the absorbent chassis 36 may be bonded to the outer cover 30 using adhesive, thermal or ultrasonic bonding techniques known to those skilled in the art. Alternatively, the absorbent chassis 36 may be connected to the outer cover 30 using conventional fasteners such as buttons, hook and loop type fasteners, adhesive tape fasteners, and the like. The other components of the diaper 20 may be suitably connected together using similar means.

As representatively illustrated in FIGS. 1–3, the absorbent chassis 36 according to the present invention may include a backsheet 52, a bodyside liner 54 which is connected to the backsheet 52 in a superposed relation, and an absorbent core 56 which is located between the bodyside liner 54 and the backsheet 52. The backsheet 52 is typically configured to hold the absorbent chassis 24 of the diaper 20 dose to the body of the wearer. In alternative configurations wherein the outer cover 30 is at least partially resistant to the flow of liquids therethrough, the backsheet 52 may optionally be omitted from the absorbent chassis 36. The absorbent chassis 36 also defines a body facing surface 50 which is configured to contact the wearer in use. Typically, the bodyside liner 54 provides the body facing surface 50.

The absorbent chassis 36 is generally conformable and capable of absorbing and retaining body exudates. The absorbent chassis 36 may have any of a number of shapes and sizes. For example, the absorbent chassis 36 may be rectangular, I-shaped or T-shaped. The size and absorbent capacity of the absorbent chassis 36 should be compatible with the size of the intended wearer and the fluid loading imparted by the intended use of the diaper 20. Typically, it is desirable that the absorbent chassis 36 have an absorbent capacity of at least about 300 grams of urine. It is generally preferred that the absorbent chassis 36 be narrower in the crotch region 26 than in the waist regions 22 and 24. It has been found that the absorbent chassis 36 of the present invention is particularly useful when the width dimension in the crotch region 26 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension of the absorbent chassis 36 allows the absorbent chassis 36 to better fit between the legs of the wearer.

The bodyside liner 54 of the absorbent chassis 36, as representatively illustrated in FIGS. 1–3, suitably presents a bodyfacing surface which is intended to be worn adjacent the body of the wearer and is compliant, soft feeling and nonirritating to the wearers skin. Further, the bodyside liner 54 may be less hydrophilic than the absorbent core 56, to present a relatively dry surface to the wearer, and may be sufficiently porous to be liquid permeable, permitting liquid to readily penetrate through its thickness. A suitable bodyside liner 54 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 54 is suitably employed to help isolate the wearer's skin from fluids held in the absorbent core 56 of the absorbent chassis 36.

Various woven and nonwoven fabrics can be used for the bodyside liner 54. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 54 comprises a nonwoven, spunbond, polypropylene fabric composed of about 2.8–3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Co. under the trade designation TRITON X-102.

The backsheet 52 of the absorbent chassis 36, as representatively illustrated in FIGS. 1–3, may suitably be composed of a material which is either liquid permeable or liquid impermeable. It is generally preferred that the backsheet 52 be formed from a material which is substantially impermeable to fluids. A typical backsheet can be manufactured from a thin plastic film or other flexible liquid-impermeable material. For example, the backsheet 52 may be formed from a polyethylene film having a thickness of from about 0.012 millimeter (0.5 mil) to about 0.051 millimeter (2.0 mils). The backsheet 52 may also comprise a film layer having a nonwoven web laminated to the outer surface thereof, such as a spunbond web of polyolefin fibers. The backsheet 52 may also be constructed of a material which is similar to the material comprising the outer cover 30, such as an STL material. Further, the backsheet 52 may be formed of a woven or nonwoven fibrous web layer which has been totally or partially constructed or treated to impart a desired level of liquid impermeability to selected regions that are adjacent or proximate the absorbent core 56. Still further, the backsheet 52 may optionally be composed of a micro-porous "breathable" material which permits vapors to escape from the absorbent core 56 while still preventing liquid exudates from passing through the backsheet 52.

The bodyside liner 54 and backsheet 52 are generally adhered to one another so as to form a pocket in which the absorbent core 56 is located to provide the absorbent chassis 36. The bodyside liner 54 and backsheet 52 may be adhered directly to each other around the outer periphery of the absorbent chassis 36 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 54 to the backsheet 52. It should be noted that both the bodyside liner 54 and the backsheet 52 need not extend completely to the outer periphery of the absorbent chassis 36. For example, the backsheet 52 may extend to the outer periphery of the absorbent chassis 36 while the bodyside liner 54 may be attached to the backsheet 52 inboard of the outer periphery of the absorbent chassis 36, or more towards the longitudinal centerline of the diaper 20. In alternative configurations, especially wherein the backsheet 52 is omitted, the bodyside liner 54 may be suitably adhered directly to the absorbent core 56.

The absorbent core 56, as representatively illustrated in FIGS. 1–3, is positioned between the bodyside liner 54 and the backsheet 52 to form the absorbent chassis 36. The absorbent core 56 is desirably conformable and capable of absorbing and retaining body exudates. The absorbent core 56 may have any of a number of shapes and sizes. For example, the composite absorbent core may be rectangular, I-shaped or T-shaped. It is generally preferred that the absorbent core 56 be narrower in the crotch region 26. The size of the absorbent core 56 should be compatible with the size of the intended wearer and the desired absorbent capacity of the absorbent chassis 36.

In a particular embodiment, the absorbent core 56 of the absorbent chassis 36 is desirably a plurality of absorbent strips which extend along the longitudinal length 58 of the absorbent chassis 36. The absorbent strips are generally rectangular in shape and define a length, a width, a thickness and a pair of opposite longitudinal side edges. The absorbent strips are configured to pivot about one of the longitudinal side edges while the opposite longitudinal side edge of the absorbent strips remains free to move. The absorbent core 56 may include any number of absorbent strips which provides the desired containment of body exudates. For example, the absorbent core 56 may include four longitudinally extending absorbent strips. In alternative configurations, the absorbent core 56 may include from 1 to about 10 absorbent strips. The arrangement of the absorbent strips provides channels between each strip to better distribute and contain fluid exudates. Moreover, the arrangement of the strips provides a greater surface area in contact with the body exudates than conventional planar absorbent cores to more effectively absorb and contain the exudates. The absorbent strips are also very conformable in the crotch section of the absorbent chassis 36. For example, the absorbent strips are arranged such that they may overlap each other in a shingled arrangement when subjected to a lateral force such as exerted by the legs of a wearer in use. Various configurations for the absorbent strips are described in U.S. patent application Ser. No. 08/476,742 of S. Gryskiewicz et al., entitled ABSORBENT ARTICLE INCLUDING LIQUID CONTAINMENT BEAMS AND LEAKAGE BARRIERS, and filed Jun. 7, 1995; the disclosure of which is hereby incorporated by reference in a manner that is consistent herewith.

The absorbent core 56 of the absorbent chassis 36 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 56 may also comprise selected blends of the various types of fibers mentioned above.

In a particular aspect of the invention, the absorbent core 56 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 56 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 56 may comprise a laminate of fibrous webs and high-absorbency material or other suitable means of maintaining a high-absorbency material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. Conglomerates of particles of high-absorbency material may also be used. An example of a superabsorbent polymer suitable for use in the present invention is a superabsorbent polymer designated IM5000 which is commercially available from Hoechst-Celanese, a business having offices in Portsmouth, Va. Other suitable high-absorbency materials may include superabsorbent polymers which are commercially available from Dow Chemical Corp., a business having offices in Midland, Mich.

As a general rule, the high-absorbency material is present in the absorbent core 56 of the present invention in an amount of from about 5 to about 95 weight percent and desirably from about 10 to about 60 weight percent based on the total weight of the absorbent core 56. The distribution of the high-absorbency material within the different portions of the absorbent core 56 can vary depending upon the intended end use of the absorbent core 56.

As representatively illustrated in FIGS. 1–3, the absorbent chassis 36 of the disposable diaper 20 may include at least one waist flap 80 which is configured to provide a barrier to the longitudinal flow of body exudates and improve the fastening of the article about the wearer. The waist flap 80 is located along one of the longitudinally opposed waist edges 40 and 42 of the absorbent chassis 36. As illustrated in FIGS. 1–3, the absorbent chassis 36 of the diaper 20 may also include a second waist flap 82 located along the opposite waist edge 40 or 42 for improved containment. The waist flaps 80 and 82 may be integral with the other portions of the absorbent chassis 36 or may be provided by separate pieces of material suitably attached to the absorbent chassis 36.

As illustrated, the waist flaps 80 and 82 generally define a length 84, a width 86, an attached edge 88, an unattached edge 90 and a pair of laterally opposed side edges 92. Desirably, the waist flaps 80 and 82 extend laterally along the entire width of the absorbent chassis 36 in the respective waist edge and define a longitudinal length of at least about 15 percent of the length of the absorbent chassis 36 to better contain the body exudates and provide improved fastening. As described below, the dual fastening system 60 of the diaper 20 may include a pair of secondary fasteners 66 and 68 which are configured to engage portions of the body facing surface 50 of the absorbent chassis or waist flap 80 or 82 in use to provide the improved fastening. The engagement of the secondary fasteners 66 and 68 with the body facing surface of the absorbent chassis 36 or waist flap 80 or 82 assists in maintaining the absorbent chassis 36 in a contacting relationship with the wearer's body in use. Desirably, each waist flap 80 and 82 is also configured such that the unattached edge 90 of the waist flaps 80 and 82 tends to position itself in a spaced relation away from the absorbent chassis 36.

The waist flaps 80 and 82 can be made from any material which provides the desired barrier against the flow of body exudates and improved fastening. For example, the waist flaps 80 and 82 may be constructed of a material which is similar to the material described above as being suitable for the backsheet 52 of the absorbent chassis 36 or the outer cover 30 of the diaper 20. Other conventional materials, such as polymeric films, may also be employed and such materials may be liquid resistant and/or gas permeable. Desirably, the waist flaps 80 and 82 are elastic or stretchable in at least the lateral direction to provide improved fastening and support of the absorbent chassis 36. For example, the waist flaps 80 and 82 may be constructed of an elastic NBL material having a basis weight of about 135 grams per square meter. Alternatively, each of the waist flaps 80 and 82 may also include at least one elastic member which is configured to gather the waist flap 80 or 82 when in use. Materials suitable for use as the elastic member of the waist flaps 80 and 82 are known to those skilled in the art. Exemplary of such materials are sheets, strands or ribbons of a polymeric, elastomeric material which are adhered to the flaps 80 and 82 in a stretched condition. Each waist flap 80 and 82 is attached to the waist edges 40 and 42 of the absorbent chassis 36 such that the waist flaps 80 and 82 provide a barrier to the lateral flow of body exudates and are configured to engage the secondary fasteners 66 and 68 for improved fastening and fit control. The attached edge 88 and side edges 92 of each of the waist flaps 80 and 82 are typically attached to the waist edges 40 and 42 and side edges 38 of the absorbent chassis 36, respectively, while the unattached edge 90 desirably remains unattached from the absorbent chassis 36 between the side edges 38 of the absorbent chassis 36. The attached edge 88 and side edges 92 of the waist flaps 80 and 82 may be attached to the absorbent chassis 36 in any of several ways which are well known to those skilled in the art. For example, the attached edge 88 and side edges 92 of the flaps 80 and 82 may be ultrasonically bonded, thermally bonded or adhesively bonded to the absorbent chassis 36.

Alternatively, as representatively illustrated in FIGS. 1–3, the waist flaps 80 and 82 may be integral with the backsheet 52 or bodyside liner 54 of the absorbent chassis 36. For example, the waist flaps 80 and 82 may be composed of portions of the backsheet 52 which extend longitudinally beyond the waist edges of the absorbent core 56 of the absorbent chassis 36. In such a configuration, the portion of the backsheet 52 extending longitudinally beyond the absorbent core 56 may be folded over upon the absorbent chassis 36 to provide the waist flaps 80 and 82.

As representatively illustrated in FIGS. 1–3, the absorbent chassis 36 of the disposable diaper 20 may include a pair of containment flaps 100 and 102 which are configured to provide a barrier to the lateral flow of body exudates. The containment flaps 100 and 102 may be located along the laterally opposed side edges 38 of the absorbent chassis 36. Each containment flap defines an attached edge 104 and an unattached edge 106. Each of the containment flaps 100 and 102 may also include at least one elongated elastic member 108 which is adhered to the unattached edge 106 of the containment flap 100 and 102 and configured to gather the unattached edge 106 and form a seal against the body of the wearer when in use. The containment flaps 100 and 102 may extend longitudinally along the entire length 58 of the absorbent chassis 36 or may only extend partially along the length of the absorbent chassis 36. When the containment flaps 100 and 102 are shorter in length than the absorbent chassis 36, the containment flaps 100 and 102 can be selectively positioned anywhere along the side edges 38 of the absorbent chassis 36. In a particular aspect of the invention, the containment flaps 100 and 102 extend along the entire length 58 of the absorbent chassis 36 to better contain the body exudates.

The containment flaps 100 and 102 can be made from any material which provides the desired barrier against the flow of body exudates. For example, the containment flaps 100 and 102 may be constructed of a material which is similar to the material comprising the outer cover 30. Other conventional materials, such as polymeric films, may also be employed which may be liquid resistant and/or gas permeable. In a particular aspect, the containment flaps 100 and 102 may be constructed of a STL material having a basis weight of about 70–75 grams per square meter and comprising a meltblown layer of meltblown polypropylene fibers between two spunbond layers of polypropylene fibers.

Each containment flap 100 and 102 is attached to the side edges 38 of the absorbent chassis 36 such that the containment flaps 100 and 102 provide a barrier to the lateral flow of body exudates. The attached edge 104 of each of the containment flaps 100 and 102 is attached to the side edges 38 of the absorbent chassis 36 while the unattached edge 106 remains unattached from the absorbent chassis 36 in at least the crotch region 26 of the diaper 20. The attached edge 104 of the containment flaps 100 and 102 may be attached to the absorbent chassis 36 in any of several ways which are well known to those skilled in the art. For example, the attached edge 104 of the flaps 100 and 102 may be ultrasonically bonded, thermally bonded or adhesively bonded to the absorbent chassis 36. In a particular aspect, the unattached edge 106 of each of the containment flaps 100 and 102 remains unattached from the side edges 38 of the absorbent chassis 36 along substantially the entire length of the unattached edge 106 to provide improved performance.

Alternatively as representatively illustrated in FIGS. 1–3, the containment flaps 100 and 102 may be integral with the backsheet 52 or bodyside liner 54 of the absorbent chassis 36. For example, the containment flaps 100 and 102 may be composed of portions of the backsheet 52 which extend laterally beyond the side edges of the absorbent core 56 of the absorbent chassis 36.

Each containment flap 100 and 102 is also configured such that the unattached edge 106 of the containment flaps 100 and 102 tends to position itself in a spaced relation away from the absorbent chassis 36 toward a generally upright and perpendicular configuration, especially in the crotch region 26 when in use. As representatively illustrated in FIGS. 1–3, the unattached edge 106 of each containment flap 100 and 102 is desirably spaced away from the absorbent chassis 36 when in use thereby providing a barrier to the lateral flow of body exudates. Desirably, the unattached edge 106 of each containment flap 100 and 102 maintains a contacting relationship with the body of the wearer while the absorbent chassis 36 may be spaced away from the body of the wearer when in use. Typically, an elastic member 108 is attached to the unattached edge 106 of each containment flap 100 and 102 to maintain the spaced away relationship between the unattached edge 106 and the absorbent chassis 36. For example, the elastic member 108 may be attached to the unattached edge 106 in an elastically contractible condition such that the contraction of the elastic member 108 gathers or contracts and shortens the unattached edge 106 of the containment flap 100 and 102.

Materials suitable for use as the elastic member 108 of the containment flaps 100 and 102 are known to those skilled in the art. Exemplary of such materials are sheets, strands or ribbons of a polymeric, elastomeric material which are adhered to the flaps 100 and 102 in a stretched condition, or which are attached to the flaps 100 and 102 while the flaps are pleated, such that elastic constrictive forces are imparted to the flaps. The elastic member 108 may also include such materials as polyurethane, synthetic and natural rubber. In a particular aspect of the invention, the elastic members 108 may be composed of a plurality of individual strands of 620 decitex LYCRA® which are commercially available from E. I. DuPont de Nemours Co. The containment flaps 100 and 102 may include from about 1 to about 10 elastic strands along the unattached edge 106. The elastic members 108 may be elongated prior to being attached to the unattached edge 106 of the containment flaps 100 and 102. For example, the elastic members 108 may be elongated at least about 75 percent and desirably from about 100 to about 150 percent before being attached such that the elastic members 108 gather the unattached edge 106 of the containment flaps 100 and 102. Desirably, the elastic members 108 are configured to gather and maintain the unattached edge 106 in a contacting relationship with the wearer's body when in use to effectively provide a seal against the lateral flow of body exudates. Alternative constructions and arrangements for containment flaps 100 and 102 are described in U.S. Pat. No. 4,704,116 issued Nov. 3, 1987, to K. Enloe the disclosure of which is hereby incorporated by reference in a manner that is consistent herewith.

The absorbent article of the different aspects of the present invention further includes a dual fastening system 60 for securing the absorbent article about the waist of the wearer which includes fasteners located on the outer cover 30 of the diaper 20 which are configured to be refastenable. The use of fasteners which are refastenable or releasably engageable allows for ease of securing and removing the diaper 20 from the waist of the wearer.

For example, the dual fastening system 60 of the present invention, as representatively illustrated in FIGS. 1–3, may include a pair of primary fasteners 62 and 64 which are located on the outermost corners of the outer cover 30 in the rear waist region 24 of the diaper 20. The primary fasteners 62 and 64 are configured to encircle the hips of the wearer and engage the outer surface 28 of the front waist region 22 of the diaper 20 for holding the diaper 20 on the wearer. Desirably, as representatively illustrated in FIGS. 1–3, the primary fasteners 62 and 64 are releasably engageable directly with the outer surface of the outer cover 30 of the diaper 20 to provide improved ease of fastening. Alternatively, the disposable diaper 20 of the present invention may include a fastening panel 70 on the outer cover 30 in the front waist region 22 of the diaper 20. In such a configuration, the primary fasteners 62 and 64 are releasably engageable with the fastening panel to maintain the diaper 20 about the waist of the wearer. When the primary fasteners 62 and 64 are releasably engaged, the side edges 32 and 34 of the outer cover 30 encircle the legs of the wearer thereby defining the leg openings. Suitable fasteners are well known to those skilled in the art and can include adhesive tape tab fasteners, hook and loop fasteners, mushroom fasteners, snaps, pins, belts and the like, and combinations thereof. For example, as representatively illustrated in FIGS. 1–3, the primary fasteners 62 and 64 may be hook type fasteners and the outer cover 30 or fastening panel 70 may be configured to function as a complimentary loop type fastener. Desirably, the primary fasteners 62 and 64 are hook type fasteners which are releasably engageable with the outer cover 30. Such an arrangement provides the ability to vary the size of the waist opening in very small increments over a wide range to fit the waist of the wearer. The primary fasteners 62 and 64 may have any shape and size which provides the desired fastening of the diaper 20 about the waist of the wearer.

The dual fastening system 60 on the disposable diaper 20 of the present invention further includes a pair of secondary fasteners 66 and 68 to provide improved securement of the diaper 20 about the waist of the wearer and to provide additional support to maintain the absorbent chassis 36 in contact with the wearer. For example, as representatively illustrated in FIGS. 1–3, the diaper 20 may include a pair of secondary fasteners 66 and 68 which are located on the side edges 32 and 34 of the outer cover 30 in the front waist region 22 of the diaper 20. The secondary fasteners 66 and 68 are configured to encircle the hips of the wearer and engage the body facing surface of the rear waist edge 42 of the absorbent chassis 36 to maintain the absorbent chassis 36 of the diaper 20 in a close conforming fit to the buttocks of the wearer. Desirably, as representatively illustrated in FIGS. 1–3, the secondary fasteners 66 and 68 are hook type fasteners which are releasably engageable directly with the body facing surface of the absorbent chassis 36 to provide improved ease of fastening. Alternatively, the disposable diaper 20 of the present invention may include one or more fastening panels (not shown) on the body facing surface of the rear waist edge 42 of the absorbent chassis 36 to which the secondary fasteners 66 and 68 are releasably engageable. When the secondary fasteners 66 and 68 are releasably engaged, the absorbent chassis 36 is supported by the secondary fasteners 66 and 68 to ensure the absorbent chassis 36 remains in close contact with the wearers buttocks in use and reduce the drooping and sagging common in conventional absorbent articles.

As discussed above, if the absorbent chassis 36 includes at least one waist flap 80, the secondary fasteners 66 and 68 may be configured to engage the body facing surface 94 of the waist flap 80 for improved performance. For example, as representatively illustrated in FIGS. 1–3, the secondary fasteners 66 and 68 may be located on the side edges 32 and 34 of the outer cover 30 in the front waist region 22 of the diaper 20 and configured to encircle the hips of the wearer and engage the body facing surface of the waist flap 80 or 82 on the rear waist edge 42 of the absorbent chassis 36 to maintain the absorbent chassis 36 of the diaper 20 in a close conforming fit to the buttocks of the wearer. In such a configuration, it is desirable that the waist flap 80 or 82 comprise a stretchable material to provide improved fastening and support for the absorbent chassis 36.

As representatively illustrated in FIGS. 1–3, the waist edges 40 and 42 of the absorbent chassis 36 and/or waist flap 80 or 82 are connected to the outer cover 30. The waist edges 40 and 42 may be connected along their entire width 86 or only along a portion of their width 86. Desirably, at least the waist edge 40 or 42 of the absorbent chassis 36 or waist flap 80 or 82 to which the secondary fasteners 66 and 68 are configured to engage is not attached along its entire width 86 such that the waist edge can flex or stretch without adversely affecting the appearance of the outer cover 30. For example, as representatively illustrated in FIGS. 1–3, the secondary fasteners 66 and 68 may be configured to releasably engage the absorbent chassis 36 or waist flap 80 in the rear waist region 24 of the diaper 20. The rear waist edge 42 of the absorbent chassis 36 or waist flap 80 may be attached only at the side edges 38 and 92 of the absorbent chassis 36 or waist flap 80, respectively, or may also be attached to the outer cover 30 along a center region. Desirably, at least about 80 percent and more desirably at least about 85 percent of the width 86 of the waist edge 42 of the absorbent chassis 36 or waist flap 82 remains unattached to the outer cover 30 for improved fastening.

The disposable diaper 20 of the different aspects of the present invention may further include elastics at the waist edges and side edges 32 and 34 of the outer cover 30 to further prevent the leakage of body exudates and support the absorbent chassis 36. For example, as representatively illustrated in FIGS. 1–3, the diaper 20 of the present invention may include a pair of leg elastic members 96 and 98 which are connected to the laterally opposed side edges 32 and 34 of the outer cover 30 in the crotch region 26 of the diaper 20. The leg elastics 96 and 98 are generally adapted to fit about the legs of a wearer in use to maintain a positive, contacting relationship with the wearer to effectively reduce or eliminate the leakage of body exudates from the diaper 20.

Materials suitable for use as the leg elastics 96 and 98 are well known to those skilled in the art. Exemplary of such materials are sheets or strands or ribbons of a polymeric, elastomeric material which are adhered to the outer cover 30 in a stretched position, or which are attached to the outer cover 30 while the outer cover is pleated, such that elastic constrictive forces are imparted to the outer cover 30. The leg elastics may also include such materials as polyurethane, synthetic and natural rubber. In a particular aspect of the invention, the elastics may be composed of individual strands of 620 decitex LYCRA elastomer which are commercially available from E. I. DuPont de Nemours Co. When individual strands of elastic are used, the waist and leg elastics may include any suitable number of elastic strands to provide containment of the body exudates. For example, the leg elastics 96 and 98 may include from 1 to 10 elastic strands. The leg elastics may be elongated prior to being attached to the outer cover 30. For example, the leg elastics may be elongated at least about 150 percent and desirably from about 200 to about 500 percent before being attached such that the elastics gather the outer cover 30 when relaxed. The leg elastics 96 and 98 may be joined to the outer cover 30 by any means known to those skilled in the art. For example, adhesive, thermal or ultrasonic bonding techniques may be used to join the elastics to the outer cover. Suitable adhesives include Findley H-2096 and H-2525A hot melt adhesives which are commercially available from Findley Adhesives, Inc.

Desirably, the leg elastics 96 and 98 extend into the waist regions 22 and 24 of the diaper 20 such that the secondary fasteners 66 and 68 are located on or adjacent to the leg elastics. For example, as representatively illustrated in FIGS. 1–3, the secondary fasteners 66 and 68 are attached to the side edges 32 and 34 of the outer cover 30 adjacent the leg elastics 96 and 98. In such a configuration, the forces exerted on the fasteners 96 and 98 by the weight of the absorbent chassis 36 are transferred to the leg elastics 96 and 98 which more evenly distribute the forces to the rest of the diaper 20. In particular, the forces are distributed through the fasteners to the waist regions and leg regions of the outer cover 30 to better support the absorbent chassis 36 of the diaper 20.

The different aspects of the present invention can advantageously provide a disposable absorbent article which has an absorbent chassis that maintains a close conforming fit with the wearer. The absorbent article also has a garment-like appearance. As a result, the disposable absorbent article of the present invention effectively contains body exudates while maintaining an optimum fit and an aesthetically pleasing appearance. Moreover, the crotch region of the disposable absorbent article of the present invention does not sag or droop as conventional absorbent articles have after becoming saturated with body exudates. As a result, the absorbent article may have a reduced level of leakage.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A disposable absorbent article which defines a front waist region, a back waist region and a crotch region which extends between and connects said waist regions, said absorbent article further comprising:

a) an outer cover;
   b) an absorbent chassis attached to said outer cover which includes a backsheet, a bodyside liner which is connected to said backsheet in a superposed relation and an absorbent core disposed between said backsheet and said bodyside liner wherein at least about 90 percent of a longitudinal length of said absorbent chassis remains substantially unattached to said outer cover; and
   c) a dual fastening system which includes:
      i) a pair of primary fasteners which are located on said outer cover in one of said waist regions of said absorbent article and which are configured to engage an outer surface of said absorbent article; and
      ii) a pair of secondary fasteners which are located on said outer cover in an opposite waist region of said absorbent article and which are configured to engage said bodyside liner of said absorbent chassis in use.

2. The absorbent article of claim 1 wherein at least about 95 percent of said length of said absorbent chassis remains substantially unattached to said outer cover.

3. The absorbent article of claim 1 wherein said primary fasteners are located on a pair of laterally opposed side edges of said outer cover in said rear waist region of said absorbent article and are configured to releasably engage said outer surface of said absorbent article in said front waist region of said absorbent article.

4. The absorbent article of claim 1 wherein said primary fasteners are hook fasteners.

5. The absorbent article of claim 1 wherein said primary fasteners are hook fasteners and are configured to releasably engage said outer cover.

6. The absorbent article of claim 1 wherein said secondary fasteners are located on a pair of laterally opposed side edges of said outer cover in said front waist region of said absorbent article and are configured to releasably engage said bodyside liner of said absorbent chassis in said rear waist region of said absorbent article.

7. A disposable absorbent article which defines a front waist region, a back waist region and a crotch region which extends between and connects said waist regions, said absorbent article further comprising:

a) an outer cover;
   b) an absorbent chassis which is connected to said outer cover in superposed relation and which defines a pair of longitudinally opposed waist edges;
   c) a waist flap connected to one of said waist edges of said absorbent chassis; and
   d) a dual fastening system which includes:
      i) a pair of primary fasteners which are located on said outer cover in one waist region of said absorbent article and which are configured to engage an outer surface of said absorbent article; and
      ii) a pair of secondary fasteners which are located on said outer cover in an opposite waist region of said absorbent article and which are configured to engage a body facing surface of said waist flap in use.

8. The absorbent article of claim 7 wherein at least about 90 percent of a longitudinal length of said absorbent chassis remains substantially unattached to said outer cover.

9. The absorbent article of claim 7 wherein said absorbent chassis defines a front attached portion and a back attached portion which are attached to said outer cover and an unattached portion which extends between and connects said attached portions and which remains substantially unattached to said outer cover.

10. The absorbent article of claim 9 wherein said unattached portion of said absorbent chassis defines a longitudinal length which is at least about 90 percent of a length of said absorbent chassis.

11. The absorbent article of claim 7 wherein said absorbent chassis includes a backsheet, a bodyside liner which is connected to said backsheet in a superposed relation and an absorbent core disposed between said backsheet and said bodyside liner.

12. The absorbent article of claim 11 wherein said backsheet and said waist flap are provided by an elastic material.

13. The absorbent article of claim 7 wherein said waist flap is an elastic material which is capable of stretching in a lateral direction.

14. The absorbent article of claim 7 wherein said waist flap defines a longitudinal length of at least about 15 percent of a length of said absorbent chassis.

15. The absorbent article of claim 7 and further comprising a second waist flap connected to an opposite waist edge of said absorbent chassis.

16. The absorbent article of claim 7 wherein said waist flap defines a pair of laterally opposed side edges which are connected to said outer cover and wherein at least a portion of said waist flap extending between said side edges of said waist flap remains substantially unattached to said outer cover.

17. The absorbent article of claim 16 wherein at least about 80 percent of a width of said waist flap remains unattached to said outer cover.

18. The absorbent article of claim 16 wherein a center region of said waist flap is attached to said outer cover and wherein portions of said waist flap extending between said center region and said side edges of said waist flap remain substantially unattached to said outer cover.

19. The absorbent article of claim 7 wherein said primary fasteners are located on a pair of laterally opposed side edges of said outer cover in said rear waist region of said absorbent article and are configured to releasably engage said outer surface of said absorbent article in said front waist region of said absorbent article.

20. The absorbent article of claim 7 wherein said primary fasteners are hook fasteners.

21. The absorbent article of claim 7 wherein said primary fasteners are hook fasteners and are configured to releasably engage said outer cover.

22. The absorbent article of claim 7 wherein said secondary fasteners are located on a pair of laterally opposed side edges of said outer cover in said front waist region of said absorbent article and are configured to releasably engage said body facing surface of said waist flap which is connected to said waist edge of said absorbent chassis in said rear waist region of said absorbent article.

23. The absorbent article of claim 7 wherein said absorbent article further comprises a pair of longitudinally extending containment flaps which are located on a pair of laterally opposed side edges of said absorbent chassis.

24. The absorbent article of claim 7 wherein said absorbent article further comprises a pair of leg elastics which are located on a pair of laterally opposed side edges of said outer cover in at least said crotch region of said absorbent article.

25. The absorbent article of claim 24 wherein said secondary fasteners are connected to said outer cover adjacent said leg elastics.

* * * * *